United States Patent [19]

Yoshii et al.

[11] Patent Number: 4,842,408

[45] Date of Patent: Jun. 27, 1989

[54] PHASE SHIFT MEASURING APPARATUS UTILIZING OPTICAL HETERODYNE TECHNIQUES

[75] Inventors: Minoru Yoshii, Tokyo; Noriyuki Nose, Sagamihara; Yukichi Niwa, Atsugi; Yoshimichi Okada, Atsugi, all of Japan

[73] Assignee: Canon Kabushiki Kaisha, Tokyo, Japan

[21] Appl. No.: 47,258

[22] Filed: May 8, 1987

[30] Foreign Application Priority Data

| | | |
|---|---|---|
| May 9, 1986 [JP] | Japan | 61-106439 |
| May 9, 1986 [JP] | Japan | 61-106440 |
| Jan. 20, 1987 [JP] | Japan | 62-010872 |

[51] Int. Cl.$^4$ ............................................. G01B 9/02
[52] U.S. Cl. ................................... 356/349; 356/351; 356/361
[58] Field of Search ........................ 356/349, 351, 361

[56] References Cited

U.S. PATENT DOCUMENTS

| | | | |
|---|---|---|---|
| 3,670,098 | 6/1972 | Korpel | 356/349 X |
| 4,340,304 | 7/1982 | Massie | 356/349 X |

OTHER PUBLICATIONS

Moore et al, "Measurement of the Optical Properties of Gradient Index Materials", *JOSA*, vol. 68, No. 9, pp. 1157-1166, 9/78.

"High-Performance Real-Time Heterodyne Interferometry," Massie et al., *Applied Optics*, vol. 18, No. 11, Jun. 1, 1979.

*Primary Examiner*—Davis L. Willis
*Assistant Examiner*—Matthew W. Koren
*Attorney, Agent, or Firm*—Fitzpatrick, Cella, Harper & Scinto

[57] ABSTRACT

A phase shift measuring apparatus for detecting a phase shift of a light wave passing through an object to be measured, including:
- supplying device for supplying first and second light waves having different frequencies;
- optical device for directing the first light wave toward the object and combining the first light wave passing through the object and the second light wave to obtain a composite light wave;
- detecting device for receiving the composite light wave and detecting a measured beat signal; and
- measuring device for comprising the measured beat signal with a predetermined reference beat signal to measure a phase shift of the first light wave.

A gradient index, a thickness distribution, and the like of an object can be obtained from the measured phase shift.

9 Claims, 7 Drawing Sheets

PHASE SHIFT MEASURING APPARATUS UTILIZING OPTICAL METERODYNE TECHNIQUES

BACKGROUND OF THE INVENTION

1. Field of the Invention

The present invention relates to a phase shift measuring apparatus according to a light wave interference method utilizing optical heterodyne techniques.

More particularly, the present invention relates to a phase shift measuring apparatus capable of highly precisely measuring a gradient index, a thickness distribution, or the like of an object to be measured upon detection of a phase shift amount of a light wave passing through the object.

2. Related Background Art

Some conventional apparatuses for detecting surface precision, thicknesses and uniformity of the quality of objects to be measured comprise interferometers such as Mach-Zehnder, Fizeau, and Twyman-Green interferometers.

In a conventional interferometer of this type, a light wave passing through an object to be measured is combined with a light wave called a reference wave to detect physical information of the object on the basis of interference fringes formed by these two light sources.

In order to detect such physical information, the interference fringes are simply observed or converted into a light intensity distribution. Alternatively, a phase shift as a function of time at each position of the interference fringes is measured as in the phase interferometer.

In order to measure a gradient index of the object by using a conventional interferometer of this type, a plane wave is caused to pass through a sample having a gradient index and a phase shift of the plane wave is converted into an intensity distribution of the interference fringes, thus measuring the gradient index. A refractive index difference $\Delta n$ can be given by the following equation:

$$\Delta n = \Delta \phi / d$$

where $\Delta \phi$ is the phase shift (i.e., phase difference) of the plane wave and d is the thickness of the sample.

The parameter for determining measurement precision is the phase difference $\Delta \phi$. According to a method of observing the interference fringes or a method of directly converting the interference fringes into a light intensity distribution, the phase difference $\Delta \phi$ cannot be detected with high precision. Although the conventional phase interferometer can detect the phase difference $\Delta \phi$ within a tolerance, the light wave phase shift as a function of time requires fine vibration of a mirror or the like with high precision. Therefore, the structure of the phase interferometer is complicated and undesirably requires a complex drive system.

A light wave interference method utilizing optical heterodyne techniques is known as a method of precisely measuring a moving speed of an object to be measured as well as the surface precision and the surface shape of the object.

Although an apparatus using the light wave interference method has an advantage in that physical information of the object can be obtained with high precision, there are a few measuring apparatuses of this type utilizing the optical heterodyne techniques.

Under these circumstances, there is no apparatus capable of simply measuring a gradient index or the like of an object to be measured with high precision.

SUMMARY OF THE INVENTION

It is an object of the present invention, in consideration of the conventional drawbacks described above, to provide a phase shift measuring apparatus for precisely measuring a gradient index or the like of the object to be measured according to an interference method utilizing optical heterodyne techniques.

It is another object of the present invention to provide a phase shift measuring apparatus for precisely measuring a gradient index or the like of the object to be measured and for easily measuring the overall characteristics (e.g., the surface precision of the object) and a position of the object according to an interference method utilizing optical heterodyne techniques.

It is still another object of the present invention to provide a phase shift measuring apparatus capable of detecting a wave having a desired intensity without increasing the beam spot of the light wave even if the object is large.

In order to achieve the above objects of the present invention, according to an aspect thereof, a phase shift measuring apparatus is characterized in that the apparatus comprises means for generating first and second light waves having different frequencies, optical means for causing one of the first and second light waves to pass through an object to be measured and combining the passed wave with the other one of the first and second light waves, and detecting means for receiving a composite light wave from the optical means to detect a phase shift of the passed light wave on the basis of a phase shift of a beat signal oscillating at the difference of the frequencies of the first and second light waves.

In order to achieve the above objects of the present invention, according to another aspect thereof, there is provided a phase shift measuring apparatus comprising: means for generating first and second light waves having different frequencies; optical means for directing one of the first and second light waves toward an object to be measured to cause the object to transmit or reflect the directed light and for combining the reflected or transmitted light wave with the other one of the first and second light waves to produce a composite light wave; detecting means for receiving the composite light wave from the optical means and detecting a phase shift of the light wave transmitted through or reflected by the object on the basis of a phase shift of a beat signal from the difference of frequencies of the first and second light waves; interference fringe forming means for radiating a third light wave having a predetermined frequency and forming interference fringes from the third light wave whose phase is shifted by the object; and monitoring means for monitoring the interference fringes.

In order to achieve the above objects of the present invention, according to still another aspect thereof, there is provided a method of measuring a phase shift, comprising the steps of: generating first and second light waves having different frequencies; producing a reference beat signal by combining the first and second light waves; producing a detected beat signal obtained such that one of the first and second light waves is transmitted through or reflected by an object to be measured, a light wave transmitted through or reflected by the object is combined with the other one of the first and second light waves, and the transmitted or reflected light wave and the object are moved relative to each other; and measuring an optical phase shift of the light wave incident on the object by using the reference and detected heat signals.

The above and other objects, features, and advantages of the present invention will be apparent from the following preferred embodiments taken in conjunction with the accompanying drawings.

DETAILED DESCRIPTION OF THE PREFERRED EMBODIMENTS

Figure 1:
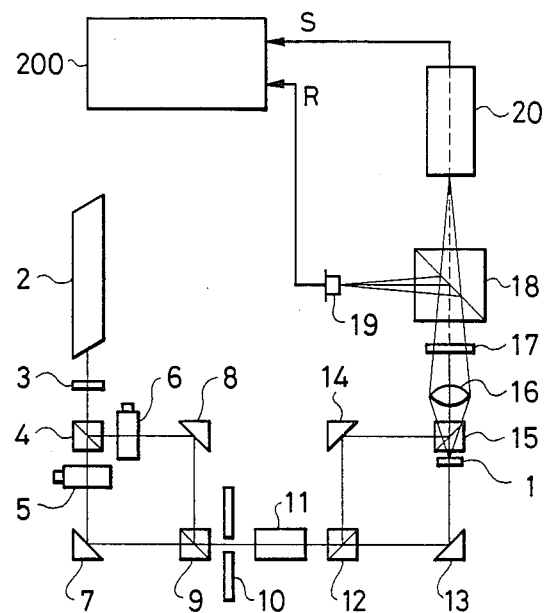
FIG. 1 is a schematic view showing an arrangement of a phase shift measuring apparatus according to an embodiment of the present invention.

FIG. 1 is a schematic view of a phase shift measuring apparatus according to an embodiment of the present invention. An object 1 to be measured is a transparent sample having a gradient index in a direction perpendicular to an optical axis of the apparatus. The object 1 comprises a plane-parallel plate. A coherent light source 2 comprises a laser. A λ/2 plate 3 causes the plane of polarization of a light beam from the coherent light source 2 to be inclined by 45° with respect to the normal to the drawing surface within a plane perpendicular to the optical axis. A polarizing beam splitter 4 (to be referred to as a PBS 4 hereinafter) splits the light beam from the λ/2 plate 3 into P- and S-components, thereby generating two light waves whose planes of polarization are orthogonal with each other. Acoustooptical elements 5 and 6 (to be referred to as A/O elements 5 and 6 hereinafter) are designed to diffract the two light waves generated by the PBS 4. Plane reflecting mirrors 7 and 8 are designed to reflect the light waves diffracted by the A/O elements 5 and 6 so as to change their optical paths, respectively. A polarizing beam splitter 9 (to be referred to as a PBS 9 hereinafter) directs the two light waves reflected by the plane reflecting mirrors 7 and 8 in one direction. An aperture 10 selectively extracts a light wave of a predetermined order from the diffracted beams generated by the A/O elements 5 and 6. A beam expander optical system 11 is designed to increase a beam spot size of the light wave. A polarizing beam splitter 12 (to be referred to as a PBS 12 hereinafter) splits the light waves again. Plane reflecting mirrors 13 and 14 are designed to reflect the two light waves split by the PBS 12 so as to change their optical paths. A polarizing beam splitter 15 (to be referred to as a PBS 15 hereinafter) combines a light wave as the S-polarized component reflected by the plane reflecting mirror 14 and the light wave as an S-polarized component reflected by the plane reflecting mirror 13 and passing through the object 1. The light wave obtained through the PBS 15 is guided by a focusing optical system 16 to detectors 19 and 20 (to be described later). The focusing optical system 16 is designed to focus the image of the object 1 on the sensor surfaces of the detectors 19 and 20. A λ/4 plate 17 is designed to circularly polarize the combined P- and S-components. A PBS 18 splits the circularly polarized beams passing through the λ/4 plate 17 and guides the split beams to the detectors 19 and 20. The detector 19 has a fixed beam incident position defined by an aperture. The detector 20 can perform one- or two-dimensional scanning. A measuring means 200 can measure a gradient index of the object 1 in accordance with signals R and S from the detectors 19 and 20. The measurement procedures of this means will be described later in detail.

Figure 2:
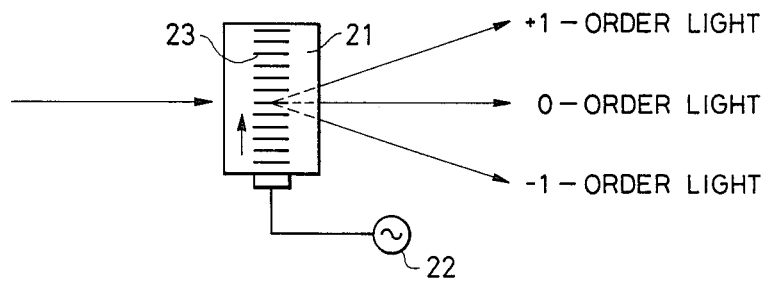
FIG. 2 is a schematic view for explaining the function of an acoustooptical (A/O) element.

FIG. 2 is a view showing the principle of operation of the A/O element 5 or 6. Each element comprises a substrate 21 made of Tellurite glass or a crystal (e.g., $TeO_2$ or $PbMoO_4$) and a driver 22 for causing the substrate 21 to generate an ultrasonic wave. A traveling wave 23 consisting of an ultrasonic wave is thus generated by the substrate 21.

In operation, the end of the substrate 21 is excited with an ultrasonic wave, the traveling wave is generated by the ultrasonic wave, and the dense/sparse refractive index pattern is generated in accordance with a wavelength of the traveling wave. Since the dense/sparse refractive index pattern has a function of a phase diffraction grating of the traveling wave, the light beam becomes incident on the traveling wave in a direction perpendicular to the traveling direction of the traveling wave, and at the same time the light wave such as a laser beam is diffracted to Doppler-shift the frequency of the light wave. The shift amount of the wave is equal to the frequency of the ultrasonic wave (traveling wave). The frequency of light wave diffracted in the traveling direction of the ultrasonic wave, that is, the frequency of +1-order light is shifted in the positive direction. However, the frequency of the light wave diffracted in a direction opposite to the traveling direction, that is, the frequency of −1-order light wave is shifted in the negative direction. Therefore, referring to FIG. 1, if the A/O elements 5 and 6 are driven with ultrasonic waves having frequencies of 80 MHz and 81 MHz, ±1-order light components of the light waves incident on the A/O elements 5 and 6 are subjected to frequency shifting of ±80 MHz and ±81 MHz, respectively. If +1-order diffracted light components are used as two light waves used for measurement, a difference between the frequencies of the first and second light waves obtained through the A/O elements 5 and 6 is given as 1 MHz.

Referring back to FIG. 1, the phase shift measuring apparatus according to this embodiment will be described in detail.

A light beam emitted from the coherent light source 2 is split into transmitted and reflected beams by the PBS 4 through the λ/2 plate 3. The reflected light is a light wave having a plane of polarization in the S direction (to be referred to as an S-polarized component hereinafter) and is linearly polarized in a direction perpendicular to the drawing surface. This light wave is subjected to diffraction by the A/O element 6. If the frequency of the ultrasonic wave generated by the A/O element 6 is given as 81 MHz and +1-order diffracted light is used, the light wave as the +1-order diffracted light (to be referred to as a first light wave hereinafter) is subjected to a frequency shift of +81 MHz and is directed toward the PBS 15 through the plane reflecting mirror 8, the PBS 9, the aperture 12, the beam expander optical system 11, the PBS 12, and the plane reflecting mirror 14 in the order named.

The light transmitted through the PBS 4 is a light wave having the plane of polarization in the P direction (to be referred to as a P-polarized component hereinafter) and is linearly polarized in a direction parallel to the drawing surface. This light wave subjected to diffraction by the A/O element 5. If a frequency of the ultrasonic wave generated in the A/O element 5 is given as 80 MHz and +1-order diffracted light is used, the light wave as the +1-order diffracted light (to be referred to as a second light wave hereinafter) is subjected frequency shifting of 80 MHz and is directed toward the PBS 15 through the plane reflecting mirror 7, the PBS 9, the aperture 10, the beam expander optical system 11, the PBS 12, the plane reflecting mirror 13, and the object 1 in the order named. Therefore, the phase of the second light wave is shifted through the object 1 according to its gradient index. A detecting wave consisting of the second light wave is combined by the PBS 15 with a reference wave consisting of the first light wave. The composite light wave passes through the λ/4 plate 17 through the focusing optical system 16 and is converted into circularly polarized components light in the opposite directions, thereby forming interference fringes on the light-receiving surfaces of the detectors 19 and 20.

The second light wave which has passed through the object 1 is combined with the first light wave of a plane wave having a 1-MHz difference from the second light wave to produce a light intensity distribution $i(x,y,t)$ defined as follows:

$$i(x,y,t) = a(x,y) + b(x,y)\cos\{2\pi \times 10^6 t + K\Delta\phi(x,y)\} \quad (1)$$

where $\Delta\phi(x,y)$ is the phase shift of the second light wave at point (x,y) of the object 1, and K is the number of waves wherein $K = 2\pi/\lambda$ (λ is the wavelength).

The phase shift $\Delta\phi(x,y)$ of the second light wave is defined as a beat signal phase shift of 1 MHz $= 2\pi \times 10^6$ (rad/s).

As described above, the first and second light waves as the circularly polarized light in the opposite directions are combined by the λ/4 plate 17, and the composite wave is split by the PBS 18 into two split beams. One of the split beams is incident on the light-receiving surface of the detector 19 having an aperture of a fixed phase (fixed position) and the other beam is incident on the detector 20 which can perform two-dimensional scanning. One-MHz beat signals are detected by the detectors 19 and 20. The light wave focused on the detector 19 comprises the first light wave and the second light wave which has passed through specific point (x0,y0) of the object 1. A 1-MHz beat signal obtained by the interference between the two light waves is detected by the detector 19 and serves as a reference signal. The light wave focused on the detector 20 consists of the first light wave and the second light wave which has passed through any point (x,y) of the object 1. A 1-MHz beat signal obtained by the interference between these two light waves at any position (x,y) is detected by scanning the detection position of the detector 20. The detected beat signal serves as a detected signal.

Figure 3:
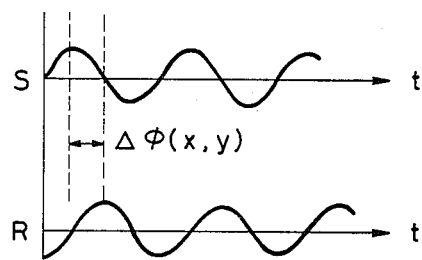
FIG. 3 is a timing chart showing a reference beat signal R and a beat signal S having phase information.

FIG. 3 shows the reference beat signal R as the reference signal output from the detector 19 and a detected beat signal S having phase information ($\Delta\phi$) and output from the detector 20. These signals are plotted along the time basis t. The detection position of the light wave in the detector 20 is one- or two-dimensionally scanned to obtain the signal shown in FIG. 3. A phase difference $\Delta\phi(x,y)$ between the detected signal S and the reference beat signal R at each position (x,y) is electrically detected to measure a relative phase shift $\Delta\phi(x,y)$ of the second light wave passing through each position (x,y) of the object 1. In other words, the gradient index of the object 1 can be measured.

Figure 4:
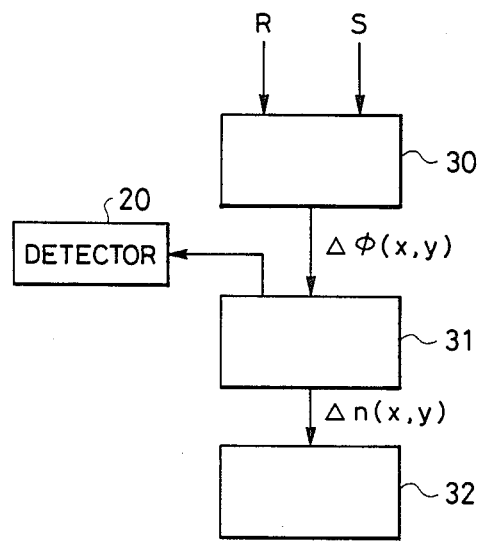
FIG. 4 is a schematic block diagram of an arrangement for measuring a gradient index in the apparatus shown in FIG 1.

FIG. 4 is a schematic block diagram for obtaining a gradient index on the basis of the beat signals R and S, showing the measurement process executed by the measuring means 200 in FIG. 1. This arrangement includes a phase detector 30, a microprocessor 31, and an output device 32 such as a CRT or a printer. The beat signals R and S generated by the detectors 19 and 20 are processed by the phase detector 30 to calculate the phase difference $\Delta\phi(x,y)$. In this case, the scanning position (x,y) of the detector 20 is designated by the microprocessor 31. Subsequently, the beat signals R and S at each scanning point (x,y) are obtained by the phase detector 30. It should be noted that the beat signal R is substantially constant. However, even if the beat signal R is changed for some reason, the reference beat signal R is processed as described above, thereby maintaining high measuring precision. A signal of the phase difference $\Delta\phi(x,y)$ detected by the phase detector 30 is A/D-converted, and the digital signal is input to the microprocessor 31. The microprocessor 31 calculates a gradient index n(x,y) from the phase difference $\Delta\phi(x,y)$ according to predetermined conversion procedures. A signal associated with the n(x,y) is output to the output device 32. The output device 32 displays numerical values or an image of the information associated with the gradient index of the object 1.

Figure 5A:
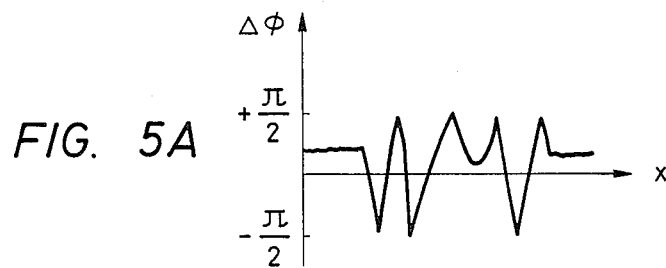
FIGS. 5A to 5D are graphs showing conversion procedures for obtaining a gradient index from phase difference data in a microprocessor.
Figure 5B:
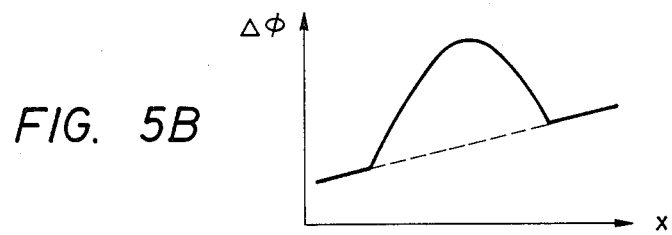
Figure 5C:
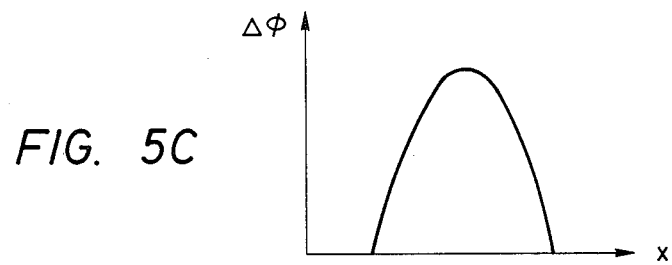
Figure 5D:
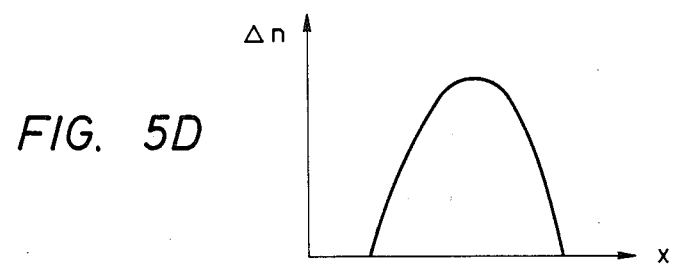

FIGS. 5A to 5D are graphs showing the conversion procedures for converting the input signals into a gradient index in the microprocessor 31. For illustrative convenience, one-dimensional (x) data is processed. However, the processing procedures are not changed in principle even if two-dimensional (x,y) data is processed. FIG. 5A shows direct data of the phase difference $\Delta\phi$. This data is measured such that the phase of the wave front of the second light wave is folded within the range of $\pm\pi/2$. Restoration of the order of the interference fringes is performed by using the folded data, thus obtaining data shown in FIG. 5B. Since noise components such as the tilt of the interferometer and nonuniformity of the thickness of the object 1 are included in the data of FIG. 5B, these components are corrected by the computer, and the distribution of the phase difference $\Delta\phi$ shown in FIG. 5C is obtained. Finally, the relative gradient index $\Delta n$ shown in FIG. 5D is obtained by using the known thickness d of the object 1 and relation $\Delta n = \Delta\phi/d$.

The detector 19 having an aperture may comprise a sensor such as an APD (Avalanche Photodiode) or a sensor as a combination of a pinhole and a PIN photodiode or a photomultiplier. The one- or two-dimensional scanning detector 20 comprises an image detector for scanning an aperture near the light incident surface, an image detector for electrically scanning each pixel, an APD arranged on a stage whose position is controllable by a computer, a combination of a pinhole and a PIN photodiode or a photomultiplier, or the like.

The A/O elements are used to obtain light waves having different frequencies in the above embodiment. However, even if elements such as black cells are used, Doppler shifting can be effected on the light waves. If a coherent light source may comprise a Zeeman laser, light beams having different frequencies can be generated by a single light source, thus simplifying the optical system.

In the above embodiment, the $\lambda/2$ plate 3 is used because the contrast ratio of the interference fringes is improved by causing the PBS 4 to split the light beam into components having identical intensities. However, instead of the $\lambda/2$ plate, the coherent light source 2 may be rotated about the optical axis such that the direction of polarization of the light beams output from the coherent light source is rotated at 45° with respect to the orthogonal planes of polarization of the PBS 4. Moreover, the PBS 18 for directing the composite light wave onto the detectors 19 and 20 may be replaced with a half mirror.

Figure 6:
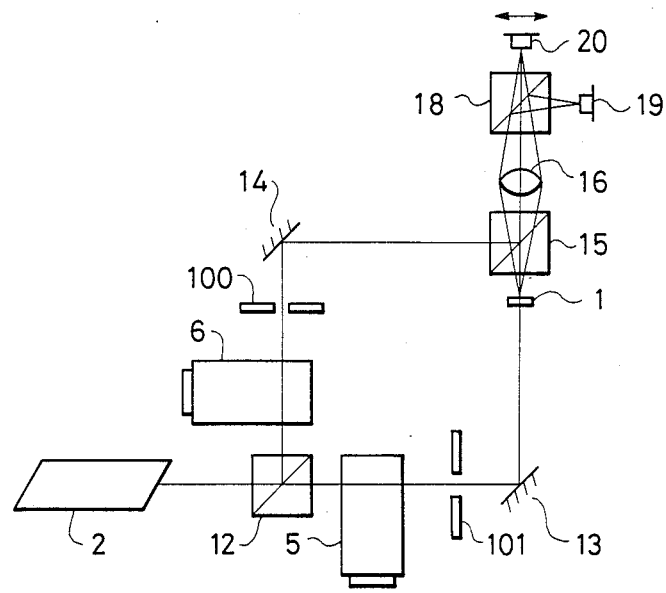
FIGS. 6 and 7 are schematic views showing phase shift measuring apparatuses according to other embodiments of the present invention, respectively.

FIG. 6 is a schematic view showing an arrangement of a phase shift measuring apparatus according to another embodiment of the present invention. The same reference numerals as in FIG. 1 denote the same parts in FIG. 6, and a detailed description thereof will be omitted. Pinholes are designated by reference numerals 100 and 101 in FIG. 6.

The apparatus of this embodiment is suitable for the case wherein a detection area of an object 1 to be measured is substantially equal to the sectional area of the spot of the beam generated by a coherent light source 2. Although the apparatus shown in FIG. 1 includes the beam expander system, the beam expander system is omitted from the apparatus of this embodiment. In the arrangement of FIG. 6, the A/O elements 5 and 6 are directly arranged within the optical path of a Mach-Zehnder interferometer. Therefore, the apparatus structure can be simplified and the number of optical elements can be reduced. Assembly time as well as adjustment time can also be greatly reduced.

Figure 7:
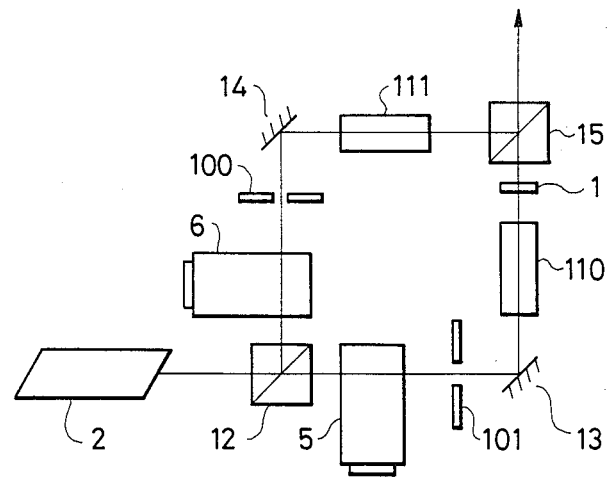

FIG. 7 shows a phase shift measuring apparatus according to still another embodiment of the present invention. The same reference numerals as in FIG. 6 denote the same parts in FIG. 7. The arrangement in FIG. 7 includes beam expander optical systems 110 and 111.

The basic arrangement of the apparatus in FIG. 7 is substantially the same as that in FIG. 6, but the apparatus in FIG. 7 is suitable for measuring an object 1 having a relatively large size as in the apparatus of FIG. 1. The beam expander optical systems 110 and 111 are arranged in optical paths of the two light waves of the Mach-Zehnder interferometer to increase the diameters of the beam spots of the light waves. Therefore, a compact, versatile measuring apparatus can be provided. The beam expander optical systems 11, 110, and 111 shown in FIGS. 1 and 7 must have low aberration levels falling within the tolerance.

In each embodiment described above, the interferometer having the optical path defined by the PBSs 12 and 15 and the plane reflecting mirrors 13 and 14 is exemplified by a so-called Mach-Zehnder interferometer. The interferometer of this type is suitable because the second light wave passes through the object only once. However, although relatively complex optical adjustments are required, a Fizeau or Twyman-Green interferometer may be utilized. In order to measure a gradient index of an object with such an interferometer, since the light wave passes the object twice through the reflecting mirror, the light wave must be controlled such that the incident position of the light wave in the forward direction must be the same as that in the reverse direction. Therefore, in order to improve measurement precision, the reflecting mirror located behind the object must come close to the object or preferably must come into contact therewith.

According to the apparatus shown in this embodiment, measurement precision of the phase shift can be expected to be improved to obtain a value as $\lambda$/several thousands, depending on sensitivity and precision of the detector. For example, if the thickness of the object is 0.1 mm and $\Delta n$ 0.1 is established, a gradient index can be obtained with repeated precision of about $10^{-5}$. Moreover, if a processing system such as a microprocessor as described above and scanning of the detector and phase detection are programmed, the gradient index can be automatically detected at high speed.

In the measuring apparatus of each embodiment, a driving mechanism such as a vibration mirror need not be used, and the overall structure of the apparatus can be simplified. In addition, measurement precision is stable.

In the phase shift measuring apparatus according to the present invention, the phase shift of the light wave passing through the object can be detected with high precision by using an optical heterodyne method. In particular, the gradient index of the object having a gradient index and the thickness distribution of the object having a thickness distribution can be measured with high precision.

The phase shift measuring apparatus according to the present invention is very suitable for measuring the gradient index of the object with high precision, as described in each embodiment. In addition to the measurement of the gradient index, a thickness distribution and surface precision of a sample having a uniform refractive index can be measured according to the above principle.

A transparent object having a gradient index has a refractive power corresponding to the gradient index. The optical path of the detection light wave is bent by the refractive power. For this reason, deviations of the measured gradient index from the actual gradient index may pose a precision problem. However, when an object having a maximum refractive index difference $\Delta n$ of about 0.1 is measured, a sample is prepared to have a thickness of $d \lesssim 0.1$, and the above deviations can be neglected.

It was therefore found that the object to be measured preferably had a gradient index and a sample thickness corresponding to about $\Delta n d \lesssim 0.01$.

If the rough values of the thickness of the object to be measured and the refractive index difference are given, measured data together with the noise data (e.g., nonuniformity of the thickness of the object and the tilt of the interferometer) can be corrected in the computer in consideration of the refraction of the detected wave in the object. Therefore, the measuring apparatus can measure any object in principle.

The interference method utilizing the optical heterodyne techniques does not require a movable optical component such as a movable mirror and allows high-precision measurement of the phase shift, thereby providing an excellent phase shift measuring apparatus. However, the conventional apparatus utilizing the optical heterodyne techniques uses a beat signal as a detecting signal obtained by superposing the light waves having different frequencies. Therefore, general physical information such as surface precision of the object cannot be known beforehand. Moreover, when the object is set in the measuring apparatus, it takes a long period of time to determine the detection position.

In the following embodiment, a phase shift measuring apparatus can be simply adjusted according to characteristics of the object and an easily position the object thereon at high speed.

Figure 8:
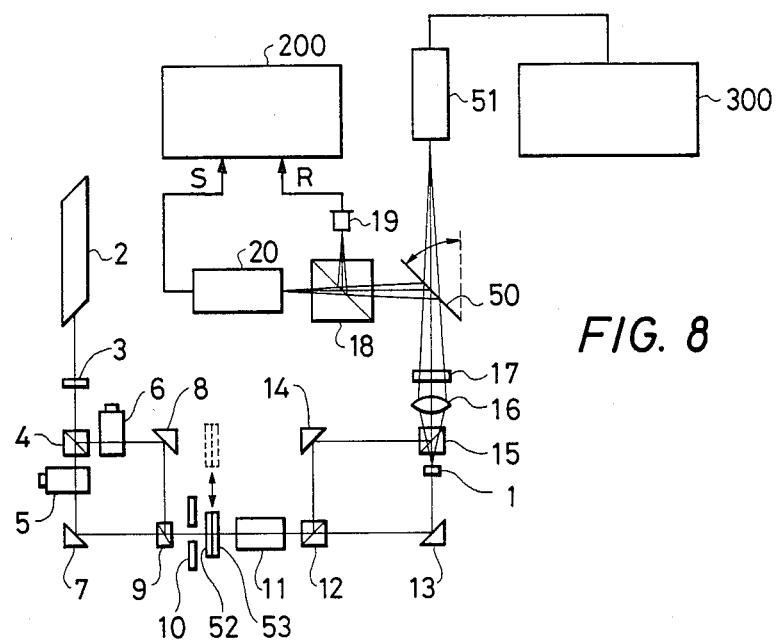
FIG. 8 is a schematic view showing a phase shift measuring apparatus having an interference fringe monitoring means according to still another embodiment of the present invention.

FIG. 8 shows a phase shift measuring apparatus having an interference fringe monitoring means according to still another embodiment of the present invention.

The same reference numerals as in FIG. 1 denote the same parts in FIG. 8. The apparatus in FIG. 8 includes a rotatable mirror 50, a TV camera 51, a polarizing plate 52, and a $\lambda/4$ or $\lambda/2$ plate (in this embodiment, a $\lambda/4$ plate is used) 53. The polarizing plate 52 is supported integrally with the $\lambda/4$ plate. The integral assembly can be inserted into or retracted from the optical path as indicated by the arrow by a mechanism (not shown). The TV camera 51 picks up interference fringes and the fringes are displayed on a display 300.

The measuring apparatus shown in FIG. 8 will be described in detail below. At first, in order to determine the position of an object 1 to be measured, the polarizing plate 52, the $\lambda/4$ plate 53, and the rotatable mirror 50 are retracted to a position indicated by the broken line in FIG. 8. The switch of a coherent light source 2 such as a laser is turned off. A focusing optical system 16 is focused such that the light-receiving surfaces of the object 1 and the TV camera 51 are conjugate with the light-receiving surfaces of detectors 19 and 20. In this case, the object 1 or the focusing optical system 16 is preferably moved along the optical axis of the system 16. After focusing is completed, the polarizing plate 52 and the $\lambda/4$ plate 53 are inserted into the optical path, and the switch of the coherent light source 2 is turned on to monitor the interference fringes (to be described below). It should be noted that the direction of polarization of the polarizing plate 53 is a direction (P direction) parallel to the drawing surface.

In this state, a light beam emitted from the coherent light source 2 is split into two beams by a PBS 4 through a $\lambda/2$ plate 3. The beam reflected by the PBS 4 is diffracted by an A/O element 6, and the beam passing through the PBS 4 is diffracted by an A/O element 5. The diffracted beams are directed toward a PBS 9 through respective plane reflecting mirrors 8 and 7. The split beams are then combined by the PBS 9 to produce a composite beam. An aperture 10 selects a diffracted component of a specific order, and the selected beam is incident on the polarizing plate 52. The beam reflected by the PBS 4 comprises a light wave as an S-polarized component. The light wave reflected by the PBS 4 is shielded by the polarizing plate 52. The light wave passed through the PBS 4 is a P-polarized component. Only the P-polarized component passes through the polarizing plate 52. Subsequently, the P-polarized component is converted by the $\lambda/4$ plate 53 into a circularly polarized wave. The circularly polarized wave is expanded by a beam expander optical system 11 and is incident through a PBS 12 on the Mach-Zehnder interferometer comprising PBSs 12 and 15 and plane reflecting mirrors 13 and 14. This light wave (to be referred to as a third light wave hereinafter) is split by the PBS 12 into the P- and S-polarized components having equal intensities. The light wave passing through the object 1 through the plane reflecting mirror 13 and the light wave reflected by the plane reflecting mirror 14 are directed toward the single optical path and are converted into circularly polarized beams having the opposite rotation angles by means of a $\lambda/4$ plate 17. These beams are superposed so as to cause an interference, and interference fringes are formed by the focusing optical system 16 on the light-receiving surface of the TV camera 51. Therefore, the observer monitors the interference fringe pattern through the TV camera 51 and determines the rough shape of the transmitted wave front corresponding to the gradient index of the object 1. Therefore, the operator can set a desired measurement position of the object 1 while monitoring the interference fringe pattern. The frequency of the third light wave used for forming the interference fringes has been Doppler-shifted by the A/O element 6. The third light wave corresponds to the first light wave used for detecting a phase shift according to an optical heterodyne method (to be described later).

As described above, the operator can determine a desired position of the object 1 while monitoring the interference fringes on the display 300 through the TV camera 51. The polarizing plate 52 and the $\lambda/4$ plate 53 are retracted from the optical path, and the rotatable mirror 50 is moved (rotated) in the optical path, i.e., the position indicated by the solid line.

In this state, the beam emitted from the coherent light source 2 is split by the PBS 4 into transmitted and reflected beams through the $\lambda/2$ plate 3. The reflected beam is a light wave having a plane of polarization in the S direction (to be referred to as an S-polarized component) and is linearly polarized in a direction perpendicular to the drawing surface. The light wave is diffracted by the A/O element 6. If a frequency of an ultrasonic wave generated by the A/O element 6 is given as 81 MHz and +1-order diffracted light is used for measurement, the light wave as the 1-order differacted light (to be referred to as a first light wave) is subjected to frequency shifting of +81 MHz. The first light wave is directed toward the PBS 15 through the parallel reflecting mirror 8, the PBS 9, the aperture 10, the beam expander 11, the PBS 12, and the plane reflecting mirror 14 in the order named.

The beam transmitted through the PBS 4 is a light wave having a plane of polarization in the P direction (to be referred to as a P-polarized component). The P-polarized component is linearly polarized in a direction parallel to the drawing surface. The P-polarized component is diffracted by the A/O element 5. If a frequency of an ultrasonic wave generated by the A/O element 5 is given as 80 MHz and +1-order diffracted light is used for measurement, the light wave as the +1-order diffracted light (to be referred to as a second light wave) is subjected to frequency shifting of +80 MHz. The second light wave is directed toward the PBS 15 through the plane reflecting mirror 7, the PBS 9, the aperture 10, the beam expander optical system 11, the PBS 12, the parallel reflecting mirror 13, and the object 1 in the order named. The phase of the second light wave has been shifted according to the gradient index of the object 1. The first and second light waves are combined by the PBS 15 and are circularly polarized in the opposite directions by the λ/4 plate 17. Therefore, the interference fringes are formed by the PBS 18 on the light-receiving surfaces of the detectors 19 and 20.

Beat signals R and S from the detectors 19 and 20 are used to measure a gradient index of the object 1 in the same manner as in the apparatus of FIG. 1, and a detailed description thereof will be omitted.

Figure 9:
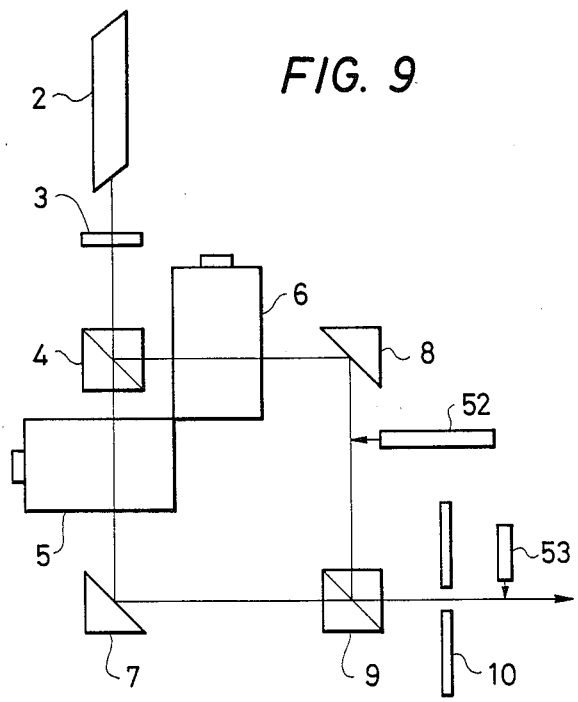
FIG. 9 is a partial view showing a modification of the apparatus shown in FIG. 8.

FIG. 9 shows a modification of the embodiment shown in FIG. 8. More specifically, FIG. 9 shows a system having the A/O elements 5 and 6 shown in FIG. 8. In other words, FIG. 9 is an enlarged view showing part of a generator for generating light waves having different frequencies. The same reference numerals as in FIG. 8 denote the same parts in FIG. 9. The arrangement in FIG. 9 includes a light-shielding plate 54.

In the embodiment of FIG. 8, one of the first and second light waves subjected to different Doppler shifting effects of the A/O elements 5 and 6 is extracted to obtain the third light wave. For this purpose, the polarizing plate 52 and the λ/2 plate 53 are used. However, according to this modification, the light-shielding plate 54 is removably inserted in the first light wave path (more specifically, between the plane reflecting mirror 8 and the PBS 9) of the first and second light wave optical paths. When the operator observes the interference fringes, the first light wave is shielded. The P-polarized second light wave passing through the PBS 9 is circularly polarized by the λ/4 plate 53 through the aperture 10, thereby obtaining the third light wave.

Figure 10:
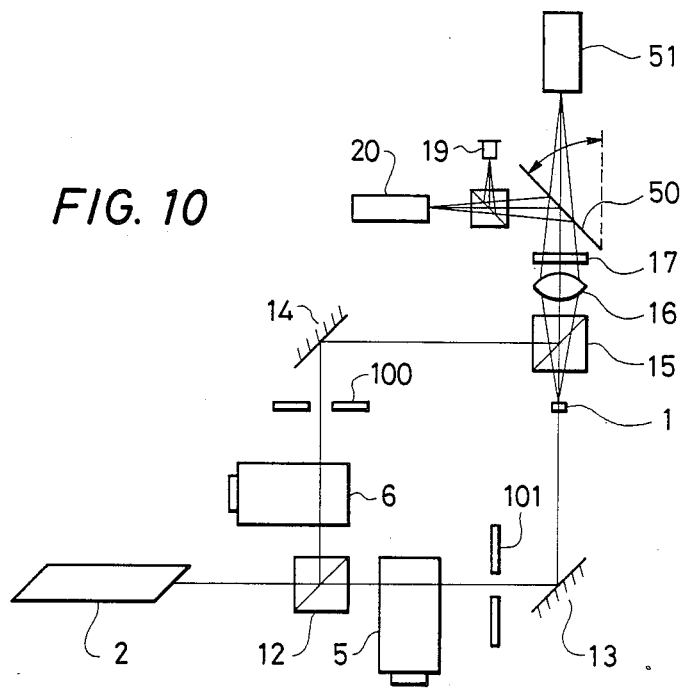
FIGS. 10 and 11 are schematic views showing phase shift measuring apparatuses having interference fringe monitoring means according to other embodiments of the present invention, respectively.

FIG. 10 shows another modification of the phase shift measuring apparatus shown in FIG. 8. The same reference numerals as in FIG. 8 denote the same parts in FIG. 10. The arrangement in FIG. 10 includes pinholes 100 and 101.

The apparatus shown in FIG. 10 is suitable for an object 1 having a size substantially equal to the size of the spot of the beam emitted from the coherent light source 2 in the same manner as in FIG. 6. Although the apparatus in FIG. 6 has the beam expander system, the beam expander system is omitted from the apparatus shown in FIG. 10. The A/O elements 5 and 6 are directly arranged in the Mach-Zehnder interferometer. Therefore, the apparatus structure can be simplified, and the number of optical elements can be reduced. Moreover, the assembly time as well as the adjustment time can be shortened.

Figure 11:
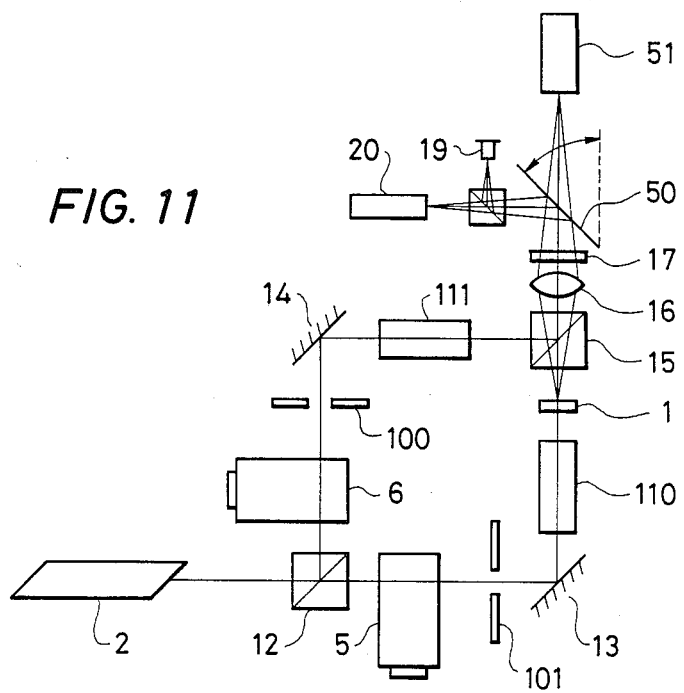

FIG. 11 shows still another modification of the phase shift measuring apparatus shown in FIG. 8. The same reference numerals as in FIG. 10 denote the same parts in FIG. 11. The apparatus in FIG. 10 includes beam expander optical systems 110 and 111.

The apparatus shown in FIG. 11 is substantially the same as that of FIG. 10, but is suitable for measuring the object 1 having the same size as in the apparatus of FIG. 8. In this modification, the beam expander optical systems 110 and 111 are arranged in the optical paths of the two light waves in the interferometer. Therefore, a compact, versatile measuring apparatus can be provided. It should be noted that the aberration levels of the beam expander optical systems 11, 110, and 111 shown in FIGS. 1 and 7 must fall within the tolerance.

In the modifications shown in FIGS. 10 and 11, the measuring position of the object 1 is determined as follows.

Drivers 22 (FIG. 2) of the A/O elements 5 and 6 are coupled to a predetermined control system (controller), and an ON/OFF command is input from the controller to the A/O elements 5 and 6 through an input interface. In order to monitor the interference fringes on the TV camera 51, the OFF signal is input to the controller to stop driving the drivers 22 of the A/O elements 5 and 6, thereby stopping diffraction of the elements. The light emitted from the coherent light source 2 directly serves as the third light wave for forming the interference fringes.

The interference monitoring method and phase shift measurement procedures according to the hererodyne techniques are the same as those in the embodiment of FIG. 1, and a detailed description thereof will be omitted.

In each embodiment or modification as described above, the interferometer having a predetermined optical path defined by the PBSs 12 and 15 and the plane reflecting mirrors 13 and 14 is constituted by a Mach-Zehnder interferometer. An interferometer of this type is suitable because the second light wave passes through the object only once. However, although relatively complex optical adjustments are required, a Fizeau or Twyman-Green interferometer may be utilized. In order to measure a gradient index of an object with such an interferometer, since the light wave passes the object twice through the reflecting mirror, the light wave must be controlled such that the incident position of the light wave in the forward direction must be the same as that in the reverse direction. Therefore, in order to improve measurement precision, the reflecting mirror located behind the object must come close to the object or preferably must come into contact therewith.

According to the apparatus shown in this embodiment, measurement precision of the phase shift can be expected to be improved to obtain a value as λ/several thousands, depending on sensitivity and precision of the detector. For example, if the thickness of the object is 0.1 mm and $\Delta n \approx 0.1$ is established, a gradient index can be obtained with repeated precision of about $10^{-5}$. Moreover, if a processing system such as a microprocessor as described above and scanning of the detector and phase detection are programmed, the gradient index can be automatically detected at high speed.

In the phase shift measuring apparatuses shown in FIGS. 8 to 11, the phase shift can be highly precisely detected according to the optical heterodyne techniques. In addition, the characteristics of the object to be measured can be monitored and observed in the form of interference fringes. The measuring position of the object can be easily detected at high speed. In particular, each measuring apparatus is suitable for measuring a gradient index of the object. The desired measuring position is subjected to high-precision measurement.

Each of the apparatuses shown in FIGS. 8 to 11 constitutes a system for detecting a phase shift of the detection light wave and allowing the operator to monitor interference fringes without increasing the size of the apparatus.

For this reason, the interference fringe light source is constituted by a light source for detecting the phase shift. For example, an interference fringe monitor light source (normally, a laser source) is separately arranged, and a coherent beam may be guided into the interferometer (the PBS 12, the reflecting mirrors 13 and 14, and the PBS 15) from the PBS 12 of the measuring apparatus shown in FIG. 8.

Figure 12:
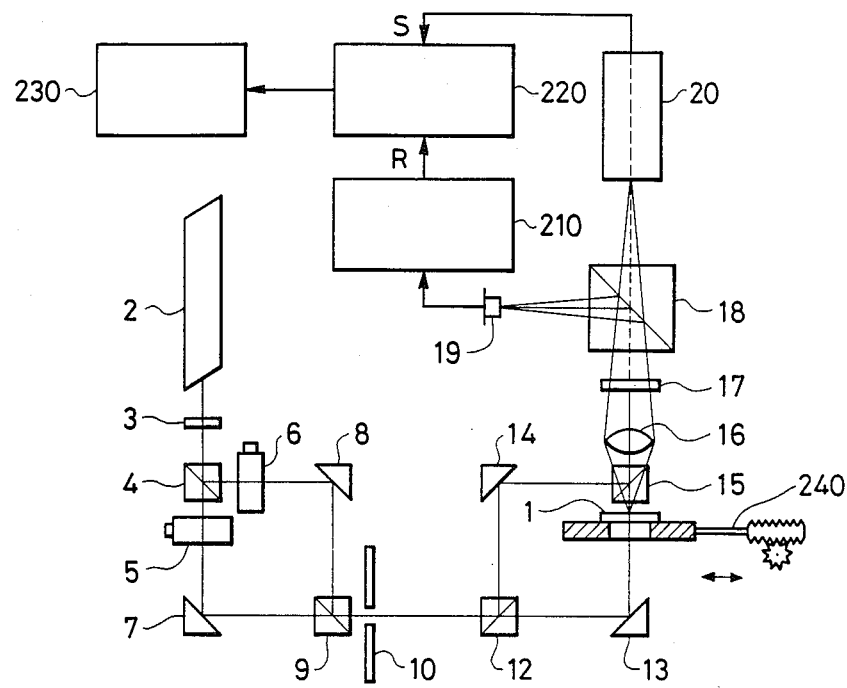
FIG. 12 is a schematic view showing a phase shift measuring apparatus having a driving means for driving a detection wave and an object relative to each other according to still another embodiment of the present invention.

FIG. 12 shows a phase shift measuring apparatus according to still another embodiment of the present invention.

The same reference numerals as in FIG. 1 denote the same parts in FIG. 12.

The apparatus shown in FIG. 12 includes a recording circuit 210 for recording an output signal from a detector 19, an operation circuit 220 for receiving signals from the recording circuit 210 and a detector 20 and calculating a phase difference therebetween, a display 230 for displaying or outputting the operation result of the operation circuit 220, and a stage 240 for carrying an object 1 to be measured. The stage can be moved in the x and y directions.

The operation of this embodiment will be described below.

A beam such as a laser beam emitted from a coherent light source 2 is split by a PBS 4 into transmitted and reflected beams through a λ/2 plate 3. The reflected beam is a light wave having a plane of polarization in the S direction (to be referred to as an S-polarized component) and is linearly polarized in a direction perpendicular to the drawing surface. This light wave is subjected to diffraction by an A/O element 6. If a frequency of an ultrasonic wave generated by the A/O element 6 is 81 MHz and +1-order diffracted light is used for measurement, the light wave as the +1-order diffracted light (to be referred to as a first light wave) is subjected to frequency shifting of +81 MHz. The first light wave is directed toward a PBS 15 through a plane reflecting mirror 8, a PBS 9, an aperture 10, a PBS 12, and a plane reflecting mirror 14 in the order named.

The beam transmitted through the PBS 4 is a light wave having a plane of polarization in the P direction (to be referred to as a P-polarized component hereinafter) and is linearly polarized in a direction parallel to the drawing surface. This light wave is subjected to diffraction by an A/O element 5. If a frequency of an ultrasonic wave generated by the A/O element 5 is given as 80 MHz and +1-order diffracted light is used for measurement, the light wave as the 1-order diffracted light (to be referred to as a second light wave) is subjected to frequency shifting of +80 MHz. The second light wave is directed toward the PBS 15 through the plan reflecting mirror 7, the PBS 9, the aperture 10, the PBS 12, the plane reflecting mirror 13, and the object 1 in the order named. Therefore, the phase of the second light wave have been shifted according to the gradient index of the object 1. This second light wave is combined with the first light wave by the PBS 15. The composite light wave is circularly polarized by a λ/4 plate 17 in the opposite directions through a focusing optical system, thereby forming the interference fringes.

The composite light wave (the first and second light waves) circularly polarized by the λ/4 plate 17 in the opposite directions is split by a PBS 18. One split beam is incident on the light-receiving surface of the detector 19 having an aperture of the fixed phase. The other split beam is incident on the detector 20. The detectors 19 and 20 detect 1-MHz beat signals. The light waves focused on the detectors 19 and 20 comprise the second light wave passing through any position (x0,y0) of the object 1 and the first light wave. The 1-MHz beat signals generated by the interference between these two light waves are the reference and detected signals detected by the detectors 19 and 20 in measurement.

In this embodiment, the reference signal obtained by the detector 19 at one measuring point is recorded in the recording circuit 210. This reference signal is compared with a detected signal obtained from the detector 20 upon movement of the stage 240 to obtain a phase difference therebetween.

More specifically, the detector 20 detects the beat signal as a detected signal at each position upon scanning the object 1 by moving the stage 240.

The phase difference between the reference signal and the detected signal is calculated by the operation circuit 220 and is displayed on the display 230.

Figure 13:
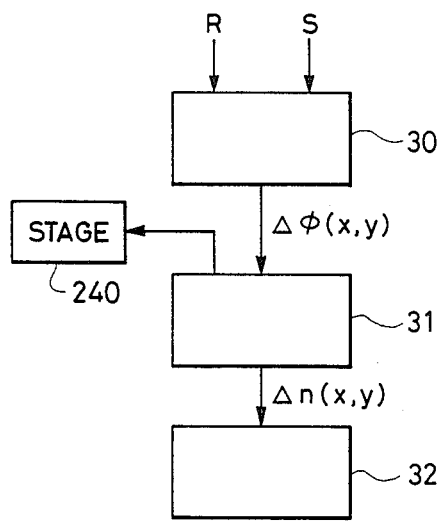
FIG. 13 is a schematic block diagram of an arrangement for measuring a gradient index of an object in the apparatus shown in FIG. 12.

FIG. 13 is a schematic block diagram of the operation circuit 220 until a gradient index is calculated on the basis of the beat signals R and S. The operation circuit 220 includes a phase detector 30, a microprocessor 31, and an output device 32 such as a CRT or a printer. The beat signals R and S generated by the detectors 19 and 20 are processed by the phase detector 30 to obtain a phase difference $\Delta\phi(x,y)$. In this case, the scanning position (x,y) of the stage 240 is designated by the microprocessor 31. The beat signals S at scanning positions (x,y) are sequentially received by the phase detector 30. In this case, the beat signal R is substantially constant.

The signal of the phase difference $\Delta\phi(x,y)$ detected by the phase detector 30 is A/D-converted, and the digital signal is input to the microprocessor 31. The microprocessor 31 calculates a gradient index n(x,y) from the phase difference $\Delta\phi(x,y)$ according to predetermined conversion procedures. A signal of the gradient index n(x,y) is output to the output device 32.

The output device 32 causes a display 230 to display information of the gradient index of the object in the form of numeric values or an image.

In this embodiment, the gradient index of the object 1 has been obtained as described above.

In addition to the measurement of the gradient index of the object, the surface shape of a lens or a reflecting mirror can be detected by detecting a phase difference between the incident light waves in the same manner as described above.

Instead of moving the object to be moved, the optical scanning means for emitting the light wave onto the object may be scanned to move the object and the measuring light wave relative to each other.

According to the present invention, there is provided a compact, high-precision optical phase difference measuring apparatus wherein the optical heterodyne interference techniques are utilized, and the object to be measured and the measuring light wave are moved relative to each other to obtain the beat signals, thereby measuring the surface shape of the object and uniformity of the medium with high precision.

In each embodiment, the profile of the object is obtained. If a refractive index of the object at an arbitrary point is known, the refractive index at each measuring point can be known according to the profile.

The generation method of the reference beat signal is not limited to the one described above, but may be obtained according to any method.

What is claimed is:

1. A phase shift measuring apparatus for detecting a phase shift of a light wave passing through an object to be measured, including:
   supplying means for supplying first and second light waves having different frequencies from each other;
   means for supplying third and fourth light waves having the same frequency;
   optical means for directing the first light wave toward the object and combining the first light wave passing through the object and the second light wave to obtain a composite light wave;
   detecting means for receiving the composite light wave and detecting a measured beat signal;
   measuring means for comparing the measured beat signal with a predetermined reference beat signal to measure a phase shift of the first light wave;
   interfering means for directing the third light wave toward the object and causing the third light wave passing through the object to interfere with the fourth light wave; and
   monitoring means for causing an operator to monitor interference fringes formed by the third and fourth light waves by said interfering means, wherein said interfering means and monitoring means are inoperative when said phase shift of the first light wave is measured.

2. An apparatus according to claim 1, further including focusing means for projecting an image of the object onto a light-receiving surface of said detecting means.

3. An apparatus according to claim 2, wherein said light-receiving surface of said detecting means can be scanned in a direction substantially perpendicular to an optical axis of said focusing means with respect to the composite light wave.

4. A phase shift measuring apparatus for detecting a phase shift of a light wave passing through an object to be measured, including:
   supplying means for supplying first and second light waves having different frequencies from each other;
   optical means for directing the first light wave toward the object and combining the first light wave passing through the object and the second light wave to obtain a composite light wave;
   detecting waves for receiving the composite light wave and detecting a measured beat signal;
   measuring means for comparing the measured beat signal with a predetermined reference beat signal to measure a phase shift of the first light wave;
   supporting means for supporting the object; and
   driving means for driving said supporting means in a direction substantially perpendicular to a travelling direction of the first light wave.

5. An apparatus according to claim 4, further including focusing means for projecting an image of the object onto a light-receiving surface of said detecting means.

6. An apparatus according to claim 5, wherein said light-receiving surface of said detecting means can be scanned in a direction substantially perpendicular to an optical axis of said focusing means with respect to the composite light wave.

7. An apparatus for measuring a gradient index of an object to be measured, said apparatus including:
   illuminating means for illuminating an object by a first light wave having a predetermined wave length;
   optical means for combining the first light wave, passing through the object illuminated by said illumination means, and a second light wave having a different wavelength from that of the first wavelength to obtain a composite light wave;
   focusing means for focusing the composite light wave, emerging from said optical means, onto first and second image positions, said focusing means having dividing means for dividing the composite light wave into first and second composite light waves, said first and second composite light waves forming respective first and second images at said first and said second positions, respectively;
   first detecting means for receiving that portion of the first composite light wave, passing through a predetermined point of the object, and detecting a beat signal of the first composite light wave, said first detecting means being positioned at said first image position;
   second detecting means for receiving those portions of the second composite light wave, passing through plural points of the object, and detecting a beat signal of the second composite light wave, said second detecting means being positioned at said second image position; and
   measuring means for measuring the gradient index of the object by comparing an output signal of said first detecting means with that of said second detecting means.

8. An apparatus according to claim 7, wherein the first and second light waves are generated by a common light source.

9. An apparatus according to claim 8, further comprising an acoustooptical element for shifting a frequency of the first light wave and that of the second light wave to different respective frequencies.

* * * * *

UNITED STATES PATENT AND TRADEMARK OFFICE
CERTIFICATE OF CORRECTION

PATENT NO. : 4,842,408
DATED : June 27, 1989
INVENTOR(S) : MINORU YOSHII, ET AL.

It is certified that error appears in the above-identified patent and that said Letters Patent is hereby corrected as shown below:

COLUMN 1

Line 3, "METERODYNE" should read --HETERODYNE--.

COLUMN 3

Line 5, "heat signals." should read --beat signals.--.

COLUMN 5

Line 53, "K$\Delta\phi$(x,y)" should read --K$\Delta\phi$(x,y)}--.

COLUMN 8

Line 31, "$\Delta$n 0.1" should read --$\Delta$n $\cong$ 0.1--.

COLUMN 10

Line 56, "1-order" should read --+1-order--.

COLUMN 13

Line 51, "1-order" should read --+1-order--.

UNITED STATES PATENT AND TRADEMARK OFFICE
CERTIFICATE OF CORRECTION

PATENT NO. : 4,842,408

DATED : June 27, 1989

INVENTOR(S) : MINORU YOSHII, ET AL.          Page 2 of 2

It is certified that error appears in the above-identified patent and that said Letters Patent is hereby corrected as shown below:

COLUMN 15

Line 50, "detecting waves" should read --detecting means--.

Signed and Sealed this

Twenty-fourth Day of April, 1990

Attest:

HARRY F. MANBECK, JR.

*Attesting Officer*          Commissioner of Patents and Trademarks